US00PP19025P2

(12) United States Plant Patent
Kordes

(10) Patent No.: US PP19,025 P2
(45) Date of Patent: Jul. 15, 2008

(54) MINIATURE ROSE PLANT NAMED 'KORBALROM'

(50) Latin Name: *Rosa hybrida*
Varietal Denomination: KORbalrom

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/787,186

(22) Filed: Apr. 13, 2007

(51) Int. Cl.
*A01H 5/00* (2006.01)

(52) U.S. Cl. ..... Plt./122

(58) Field of Classification Search ..... Plt./122
See application file for complete search history.

(56) References Cited

PUBLICATIONS

QZ (CPVO) Application # 2006/0367, Apr. 15, 2006, W. Kordes' Söhne Rosenschulen GmbH & Co KG.

*Primary Examiner*—Kent L. Bell
*Assistant Examiner*—S. B. McCormick-Ewoldt

(57) ABSTRACT

A new and distinct variety of miniature rose with long lasting, novel pink flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORbalrom'.

BACKGROUND OF THE INVENTION

The new variety of rose plant of the present invention originated from a controlled crossing during the summer of 2002 in a breeding program between 'Poulsabel' (U.S. Plant patent application Ser. No. 10/683,876-now abandoned) and an 'un-named seedling'.

The resulting seeds were planted in a glasshouse during the following winter, subsequently germinated and grew. The resulting seedlings exhibited distinctive physical and biological characteristics. The new rose plant was selected in as a single plant from the seedling beds due to its superior characteristics and asexually propagated for further evaluation. This new and distinctive rose variety is named 'KORbalrom'.

SUMMARY OF THE INVENTION

GENUS, SPECIES AND VARIETY DENOMINATION

The botanical classification of the new rose plant is *Rosa hybrida,* 'KORbalrom'.

BACKGROUND OF THE INVENTION

The new variety of miniature rose plant of the present invention originated from a controlled crossing in a breeding program between the non patented rose variety 'Poulsabel' and an 'un-named seedling', which was developed by the same inventor.

The hybridization, seed production, seed germination, seedling selection, and subsequent propagations were conducted in controlled greenhouse environments. The new rose plant was selected as a single plant from the seedling beds due to its superior characteristics and asexually propagated for further evaluation. This new and distinctive miniature rose variety is named 'KORbalrom'.

SUMMARY OF THE INVENTION

The new rose plant may be distinguished from its seed parent, 'Poulsabel', by the following combination of characteristics:

1. 'KORbalrom' has hot pink colored flowers while the seed parent has dark red flowers; and
2. 'KORbalrom' is compact and suitable for 10.5 cm pot production while the seed parent is significantly larger and suitable for 15 cm production.

The new rose plant may be distinguished from its pollen parent, an 'un-named seedling' by the following combination of characteristics:

1. 'KORbalrom' has hot pink colored flowers while the seed parent has medium red flowers; and
2. 'KORbalrom' is compact and suitable for 10.5 cm pot production while the pollen parent is significantly larger and suitable for 15 cm production.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORbalrom' from all other varieties of which we are aware.

As part of the rose development program, Tim-Hermann Kordes germinated the seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORbalrom' was selected in May, 2003 from the seedling beds to be asexually propagated for further evaluation. The first asexual reproduction of 'KORbalrom' was done by rooting softwood cuttings in July, 2003 at the Rosa-Danica Nursery in Odense, Denmark.

This initial and other subsequent propagations conducted in controlled environments show that the foregoing and all other characteristics of 'KORbalrom' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORbalrom'. Specifically illustrated in SHEET ONE are flower buds, an open bloom, detached petals, detached sepals, stems, and several leaves.

DETAILED BOTANICAL DESCRIPTION

The following is a description of 'KORbalrom', as observed in its growth in March, 2007 in a greenhouse in Jackson County, Oregon on plants of 9 months of age. Color references are made using The Royal Horticultural Society (London, England) Colour Chart, 2001 except where common terms of color are used.

For a comparison, several physical characteristics of the rose variety 'KORmisso', a rose variety from the same inventor described and illustrated in U.S. Plant Pat. No. 11,264 and issued on Mar. 7, 2000 are compared to 'KORbalrom' in Chart 1.

CHART 1

| | 'KORbalrom' | 'KORmisso' |
|---|---|---|
| Sepals | Weak foliaceous appendages. | Normal to heavily appendaged. |
| Petals | Normally 75 petals. | Normally 50-60 petals. |

Parents:

*Seed parent.*—'Poulsabel'.

*Pollen parent.*—'Un-named seedling'.

Classification:

*Botanical classification.*—*Rosa hybrida,* 'KORbalrom'.

*Commercial classification.*—Miniature rose.

FLOWER AND FLOWER BUD

Blooming habit: Recurrent. Blooms are uniform in height and size.

Flower bud:

*Size.*—Upon opening, 25 mm in length from base of receptacle to end of bud and 15 mm in diameter.

*Bud form.*—Medium length. Globular.

*Bud color.*—As sepals first unfold, bud color is Red-Purple Group 59B. When ¼ open, the upper surface of petals is Red-Purple Group 63B, and the lower surface is Group Red-Purple Group 61B.

*Sepals.*—Size: Average 25-30 mm long×7-9 mm wide. Shape: Sepals generally subulate. Sepal apex is generally cirrose. Weak foliaceous appendages on three of the five sepals. Base is flat at union with receptacle. Quantity: Five. Surface texture: Upper and lower surfaces: Numerous small white hairs. Limited numbers of stipitate glands on those sepals with foliaceous appendages. Color: Upper surface: Green Group 137A. Lower surface: Green Group 137A. Intonations of Greyed-Purple Group 183C upon opening, then diminishing.

*Receptacle.*—Surface: Smooth. Color: Green Group 138A. Shape: Broad funnel shaped. Size: 6-8 mm (h)×10-12 mm (w).

*Peduncle.*—Surface: Smooth, except for a few stipitate glands. Length: 40-50 mm average length. Diameter: 3-4 mm average diameter. Color: Green Group 138A. On juvenile stems, intonations of Greyed-Purple Group 183C. Not observed on mature stems. Strength: Strong. Borne: 1-4 buds per flowering stem.

Flower bloom:

*Fragrance.*—Light floral fragrance.

*Duration.*—Long lasting. A blooming plant with flowers has a commercial shelf life in excess of 20 days.

*Size.*—Medium to large for a 10.5 cm pot rose. Average flower diameter is 50-55 mm when open.

*Form.*—Shape of flower when viewed from the side: Upon opening, upper part: Flat. Upon opening, lower part: Concave. Open flower, upper part: Flattened convex. Open flower, lower part: Flat.

Color:

*Upon opening, petals.*—Outermost petals: Outer Side: Red-Purple Group 60C. Inner side: Red-Purple Group 61C. Innermost petals: Outer Side: Red-Purple Group 60C. Inner Side: Red-Purple Group 61C.

*Upon opening, basal petal spots.*—Basal petal spot, outermost petals: Outer Side: White Group N155C. Inner Side: Yellow-Orange Group 23D. Basal petal spot, innermost petals: Outer Side: Yellow-Orange Group 23C. Inner Side: Between Yellow-Orange Group 23B and 23C.

*After opening, petals.*—Outermost petals: Outer Side: Red-Purple Group 60D. Inner Side: Red-Purple Group 61C. Innermost petals: Outer Side: Red-Purple Group 60D. Inner Side: Red-Purple Group 61C.

*After opening, basal petal spots.*—Basal petal spot, outermost petals: Outer Side: White Group N155C. Inner Side: Green-Yellow Group 1C. Basal petal spot, innermost petals: Outer Side: Green-Yellow Group 1C. Inner Side: Yellow-Orange Group 23D.

General Tonality: Petal colors uniform. On open flower Red-Purple Group 61C. No change in the general tonality at the end of the $10^{th}$ day. Afterwards, general tonality is Red-Purple Group 61D.

Petals:

*Petal count.*—Very double. Approximately 75 petals under normal conditions.

*Petal reflex.*—Petals reflex somewhat.

*Petal edge.*—Entire.

*Petal shape.*—Apex shape is round. Shape of base is round to broadly deltoid.

*Petal size.*—25 mm long; 22-26 mm wide.

*Thickness.*—Thick.

*Petal arrangement.*—Regular pattern with overlapping edges.

*Petaloids.*—Present. Average of 10-15 per flower. Petaloids are 15 mm long and 12 mm wide. Color of inner side is Red-Purple Group 61D. Color of outer side is Red-Purple Group 61C. Surface texture is rough and crinkled. Shape is linear to round.

Reproductive organs:

*Pistils.*—Abundant. Approximately 65-75 present. Stigmas: Location: Outermost stigmas are at same position as anthers, center stigmas are superior in position. Color: Green-White Group 157B. Styles: Length: 10 mm long. Color: Green-White Group 157B.

*Stamens.*—Approximately 110 and regularly arranged around the flower. Anthers: Size: 2-3 mm long. Color: Yellow-Orange Group 23D. Pollen: Limited. Color: Yellow-Orange Group 17C. Filaments: Color: Yellow-Orange Group 17C. Length: 3 mm.

THE PLANT

*Plant growth.*—Moderate vigor. Upright to bushy habit. When grown as a 15 cm nursery plant, the average height of the plant itself is 25 cm and the average width is 18 cm.

*Stems.*—Stem color: Young wood: Green Group 137B. Older wood: Green Group 137B. Stem surface: Young wood: Smooth. Older wood: Smooth.

*Prickles.*—Present. Incidence: Upper half of plant thornless or nearly so. Most stems of basal origin having small thorns on the lower half of the stem, where density is up to 5 per 10 cm of stem. Size: Average length: 5 mm. Color: Immature prickles: Greyed-Red Group 179D. Mature prickles: Greyed-Red Group 173D. Senescing to Greyed-Orange Group 164C. Prickles on juvenile portions of the plant may exhibit intonations of Greyed-Red Group 179C. Shape: Downward hooked.

*Leaves and leaflets.*—Normally 5 leaflets on normal leaves in middle of the stem. Average abundance. Leaf size: 110 mm (l)×60 mm (w). Quantity: Abundant. Texture: Semi-glossy and smooth above. Matte and smooth below. Color, mature foliage: Upper Leaf Surface: Between Green Group 137A and Yellow-Green Group 147A. Lower Leaf Surface: Yellow-Green Group 147B. Color, juvenile foliage: Upper Leaf Surface: Green Group 137A. Lower Leaf Surface: Green Group 138A. Anthocyanin intonation: Present. Greyed-Red Group 179B. Location: Intonations present on juvenile stems, thorns, leaflet margins, rachis, and stipules.

*Stipules.*—Size: 15 mm (l)-4 mm (w). 12 mm wide at the tips. Stipule color: Green Group 137A. On juvenile leaves, intonations of Greyed-Red Group 179B. Presence of stipitate glands: Present on margins. Margins: Serrated.

*Petiole.*—Length: 30 mm-35 mm average. Diameter: 1.5 mm average diameter. Petiole color: Green Group 137A. Anthocyanin: Present. Greyed-Red Group 179B. Underneath: Smooth. Prickles: 1-2 small prickles underneath. Stipitate glands: Present on margins.

*Petiole rachis.*—Length: 30mm-35 mm average. Diameter: 1.5 mm average diameter. Petiole color: Green Group 137A. Anthocyanin: Present. Greyed-Red Group 179B. Underneath: Smooth. Prickles: 1-2 small prickles underneath. Stipitate glands: Present on margins.

*Leaflets.*—Size: Average size of the terminal leaflet is 40 mm (l)×30 mm (w). Color: Upper side: Green Group 137A. Lower side: Green Group 138A. Shape: Base: Broadly ovate. Apex: Acute. Leaflet: Pointed oval. Surface: Semi-glossy above. Matte surface below. Margins: Finely serrated. Texture: Medium thickness.

Hips/seed formation: None observed. The plant has not been grown to the stage of hip and seed development due to its use as a flowering potted plant.

Winter hardiness: Due to the variety's principal use in greenhouses, winter hardiness has not been evaluated.

Disease resistance: Above average resistance to *Botrytis* under normal growing conditions.

I claim:

1. A new and distinct variety of miniature rose plant characterized by the following combination of characteristics:

(a) forms abundant, attractive long lasting pink flowers;

(b) exhibits a compact and bushy growth habit;

(c) is suited for growing in greenhouse in pots from softwood cuttings, and;

(d) exhibits durable flowers and foliage suitable for distribution in the floral industry;

substantially as herein illustrated and described.

* * * * *

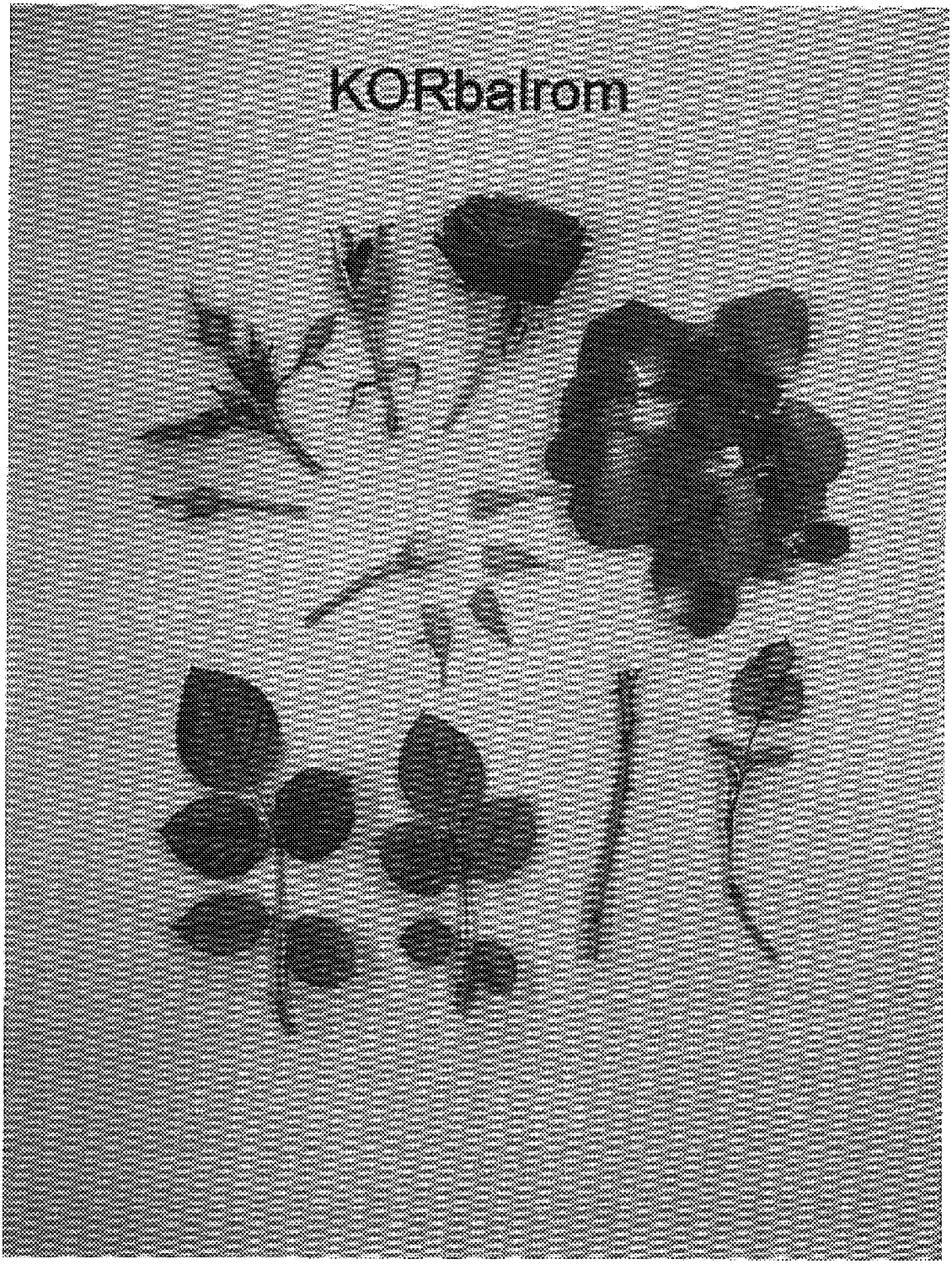
KORbalrom